United States Patent
Werblin et al.

(10) Patent No.: US 10,639,142 B2
(45) Date of Patent: May 5, 2020

(54) MULTICOMPONENT INTRAOCULAR LENS

(71) Applicant: INFINITEVISION OPTICS, Strasbourg (FR)

(72) Inventors: Ted Werblin, Princeton, WV (US); Philippe Kuhn, Strasbourg (FR)

(73) Assignee: INFINITEVISION OPTICS, Strasbourg (FR)

( * ) Notice: Subject to any disclaimer, the term of this patent is extended or adjusted under 35 U.S.C. 154(b) by 0 days.

(21) Appl. No.: 15/641,977

(22) Filed: Jul. 5, 2017

(65) Prior Publication Data

US 2017/0296331 A1 Oct. 19, 2017

Related U.S. Application Data

(63) Continuation of application No. PCT/EP2016/050081, filed on Jan. 5, 2016.

(30) Foreign Application Priority Data

Jan. 6, 2015 (EP) .................................... 15150142

(51) Int. Cl.
*A61F 2/16* (2006.01)
*A61F 2/14* (2006.01)

(52) U.S. Cl.
CPC .......... *A61F 2/1648* (2013.01); *A61F 2/1664* (2013.01); *A61F 2/15* (2015.04);
(Continued)

(58) Field of Classification Search
CPC .................. A61F 2/1694; A61F 2/1648; A61F 2002/16902
See application file for complete search history.

(56) References Cited

U.S. PATENT DOCUMENTS 5,366,502 A * 11/1994 Patel ..................... A61F 2/1602
  623/6.27
5,968,094 A * 10/1999 Werblin ................ A61F 2/1602
  623/6.27
(Continued)

FOREIGN PATENT DOCUMENTS

DE   20 2013 009 162 U1   2/2014
JP       06-048620 U      7/1994
(Continued)

OTHER PUBLICATIONS

International Search Report and Written Opinion of International Patent Application No. PCT/EP2016/050081 dated Apr. 7, 2016.
(Continued)

*Primary Examiner* — David H Willse
*Assistant Examiner* — Javier G Blanco
(74) *Attorney, Agent, or Firm* — Arent Fox LLP

(57) ABSTRACT

A multicomponent intraocular lens implantable in an optical system of a human eye, comprising: a base component and a front component, the front component comprising an attachment tab which extends from a circumferential side of the optical portion of the front component and engages the flange for attaching the front component to the base component, wherein the attachment tab of the front component comprises a resilient projection that protrudes away from the optical portion beyond the flange, wherein a portion of the resilient projection is located at a non-overlapping position with respect to the haptic of the base component in a circumferential direction around the optical portions, wherein the portion of the resilient projection has a back surface which is located backwards from a front surface of the haptic of the base component in the thickness direction of the base component.

17 Claims, 5 Drawing Sheets

(52) U.S. Cl.
CPC ....... *A61F 2/1645* (2015.04); *A61F 2002/169* (2015.04); *A61F 2002/1681* (2013.01); *A61F 2002/16902* (2015.04); *A61F 2220/0008* (2013.01); *A61F 2220/0033* (2013.01); *A61F 2230/0013* (2013.01)

(56) References Cited

U.S. PATENT DOCUMENTS

| | | | | |
|---|---|---|---|---|
| 2004/0106993 | A1* | 6/2004 | Portney | A61F 2/1648 623/6.43 |
| 2008/0215147 | A1* | 9/2008 | Werblin | A61F 2/1648 623/6.34 |
| 2009/0279048 | A1* | 11/2009 | Hong | A61F 2/1613 351/159.21 |
| 2011/0264212 | A1* | 10/2011 | Basoglu | A61F 2/14 623/6.51 |
| 2012/0078363 | A1* | 3/2012 | Lu | A61F 2/1635 623/6.37 |
| 2013/0053955 | A1* | 2/2013 | Currie | A61F 2/1629 623/6.17 |
| 2013/0304203 | A1* | 11/2013 | Beer | A61F 2/1624 623/6.37 |

FOREIGN PATENT DOCUMENTS

| | | |
|---|---|---|
| JP | 2009-509636 A | 3/2009 |
| JP | 2010-516394 A | 5/2010 |
| WO | WO-2007/040964 A1 | 4/2007 |
| WO | WO 2008/094518 A1 | 8/2008 |
| WO | WO 2011/006008 A1 | 1/2011 |
| WO | WO 2012/054854 A2 | 4/2012 |

OTHER PUBLICATIONS

Communication from the Japanese Patent Office in counterpart application No. 2017-553458, dated Dec. 3, 2019.

* cited by examiner

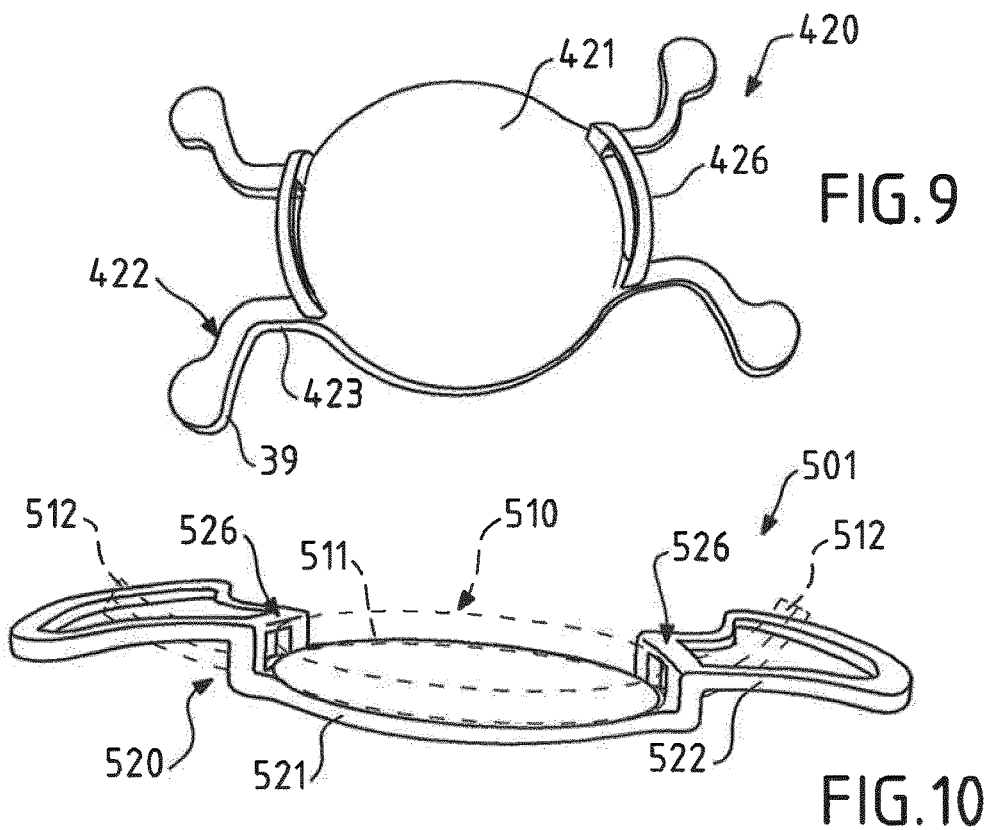
FIG.9
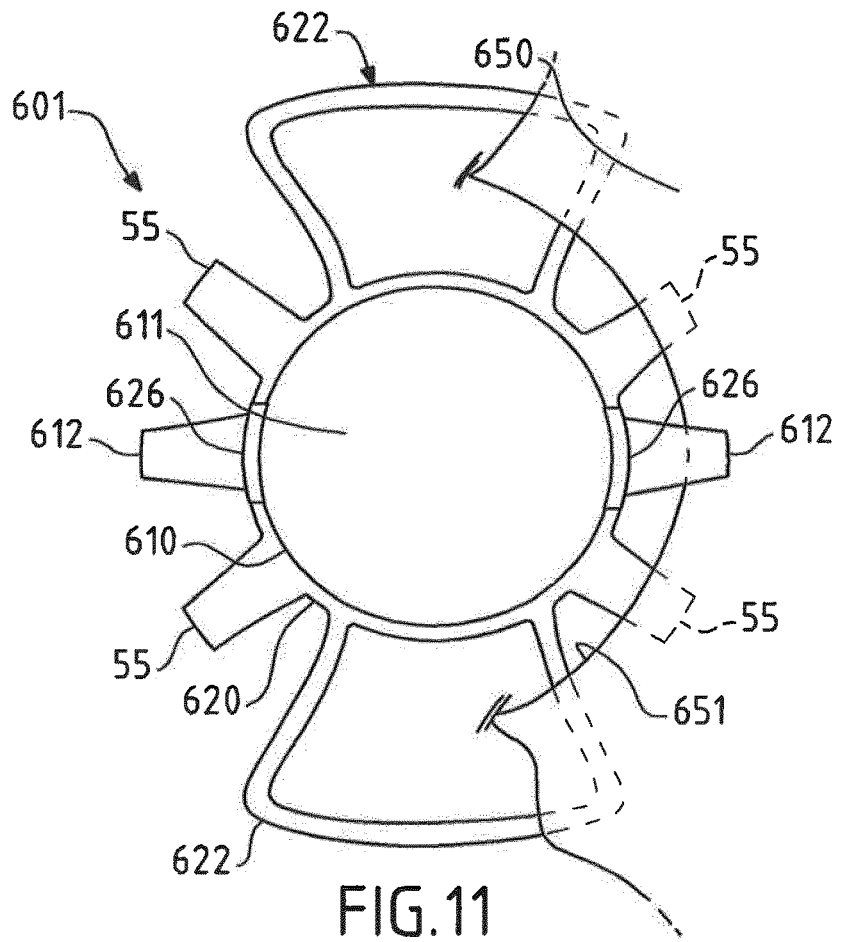
FIG.10
FIG.11

MULTICOMPONENT INTRAOCULAR LENS

CROSS-REFERENCE TO PRIORITY APPLICATIONS

This application is a Bypass Continuation of International Patent Application No. PCT/EP2016/050081, filed Jan. 5, 2016, which claims priority to European Patent Application No. 15150142.6, filed Jan. 6, 2015. The disclosures of the priority applications are incorporated in their entirety herein by reference.

FIELD OF THE INVENTION

The invention relates to the technical field of multicomponent intraocular lenses implantable in an optical system of a human eye for correction of visual disabilities.

BACKGROUND

Cataract refers to a medical deficiency of the eye due to loss of transparency of the crystalline lens. An accepted treatment for this condition is surgical removal of the crystalline lens and replacement by an artificial intraocular lens.

Multicomponent intraocular lenses (MC-IOL) for use in refractive cataract surgery are known in the art as illustrated e.g. by publications WO-A-2008094518, WO-A-2011006008 and WO-A-2012054854. A multicomponent intraocular lens includes a base component suitable for posterior chamber implantation and at least one front component that is detachably attached to the base component and that can be modified by either exchanging the front component or by altering the refractive properties in vivo at any post-operative time. The above-described structure permits the base component to form a platform upon which the at least one front component is placed and attached in a releasable manner. During routine cataract surgery, the MC-IOL replaces the crystalline lens of the human eye. Once a patient's eye has healed after such a surgery, the surgeon reenters the eye and modifies or replaces the front component, if necessary, to modify the optical characteristics of the eye until the desired levels for each optical characteristic are attained.

MC-IOLs that are designed specifically to permit the easy exchange of front optical components at a post-operative period involve considerable benefits in terms of visual correction. This is because the actual surgery of implanting the lens in the first place, as well as variances in the manner in which the eye heals after implantation, potentially create distortions which may not stabilize for several months after the operation. Therefore, the ability to measure and to compensate for the distortions optimally takes place several months after surgery and cannot typically be predicted prior thereto. Since the same surgical wound may be used for both the primary and secondary operations, additional distortion due to wound healing would not be anticipated as a result of the second operation. Furthermore, the ability to exchange optical components of a multicomponent intraocular lens can be economical compared to removing, modifying, and re-implanting a single component lens, as well as easier to perform.

The MC-IOL concept allows for adjustments or enhancement operations, beyond its use in primary cataract surgery to compensate for any miscalculation or any biological variability or any change in the condition of the eye over time after the primary operation. In order for these surgical adjustments to be workable, the surgeon must have easy access to the front component. To assure this, the front component must be left out of the capsule, in the sulcus. On the other hand, the base component is left in the capsule.

In a prior art MC-IOL, the edges of the capsule are placed between the haptics of a front lens assembly and an underlying base lens. Vertically extending flanges of the base lens and their corresponding slots allow a space between the haptics of the front lens assembly and the base lens, so that a special instrument, referred to as a capsule snare, allows the surgeon to place the front lens assembly haptic above the edges of the capsule. The vertically extending flanges and corresponding slots position the front lens assembly in front of or away from the capsule, that is, in the sulcus, making surgical removal and replacement of the front lens assembly very safe and technically simple. Put another way, the flanges and slots assure easy removal and replacement of the front lens assembly during an enhancement operation, despite the normal healing process that involves capsule contracture around the base component.

DE-U-202013009162 discloses an intraocular lens assembly comprising an intraocular lens structure for implantation in a capsular bag of an eye. The IOL comprises an optical structure having a periphery, at least two rear supports connected to the periphery and extend away therefrom, intended to be within the capsular bag when the IOL is implanted in the capsular bag, and at least two front legs connected to the periphery of the optical structure and extend away therefrom, intended to be located outside of the capsular bag. The front legs and the rear supports hold a front capsular bag between them. In an embodiment, the intraocular lens assembly further comprises a secondary intraocular lens for attachment to a front side of the IOL. The S-IOL comprises a secondary optical structure 35 and at least two fixing portions 37 each of which is intended to cooperate with one of the said front supports 8 to secure the S IOL to the IOL. In an embodiment, the capsular bag can be clamped between a front surface of the rear supports and a rear surface of the fixing portions 37.

The primary problem of this configuration is the difficulty or impossibility to rotate the lenses combination once they are assembled together because the tabs have captured the capsule edge and cannot be easily disengaged. Indeed, in case of a toric correction, orientation is determined and must be modified by the surgeon in the eye of the patient during surgery by rotating the elements inside the capsular bag when both lenses are assembled together. When assembled together, the system of DE-U-202013009162 will create a tension on the capsulorhexis which may prevent lens rotation, and thus, not allowing for proper axis orientation. In other words, it is not possible to manipulate such lens system inside the capsular bag to properly orient the lens axis.

SUMMARY

A significant problem occurring with IOLs is the rotation away from its intended axis. This is mainly due to the shape of the IOLs, and especially the haptics, which are unable to prevent the IOL from rotating within the capsular bag. Indeed, the circular shape of most haptics is designed to fit to the dimensions of the capsular bag, which is also circular and thus, does not offer resistance.

One objective of the present invention consists in providing an MC-IOL achieving improved stability when used in a posterior chamber implantation, in particular improved orientation stability of the MC-IOL.

In an embodiment, the invention provides a multicomponent intraocular lens implantable in an optical system of a human eye, the multicomponent intraocular lens comprising:
a base component having a front surface intended to be turned towards a front side of the human eye and a back surface opposed to the front surface in thickness direction of the base component and intended to be turned towards a back side of the human eye, the base component comprising a central portion and a haptic which extends from a circumferential side of the central portion away from the central portion, the base component further comprising a retaining member located at a periphery of the central portion and protruding on the front surface of the base component, and a front component comprising an optical portion arranged in front of the front surface of the optical portion of the base component, the front component further comprising an attachment tab which extends from a circumferential side of the optical portion of the front component away from the optical portion and engages the retaining member for attaching the front component to the base component,
wherein the attachment tab of the front component comprises a resilient projection that protrudes away from the optical portion beyond the retaining member, wherein a portion of the resilient projection is located at a non-overlapping position with respect to the haptic of the base component in a circumferential direction around the optical portions, wherein the portion of the resilient projection has a back surface which is located backwards from a front surface of the haptic of the base component in the thickness direction of the base component.

Thanks to these features, it is possible to constrain the rim of the capsular bag between the haptic or haptics of the base component installed within the capsular bag and the adjacent resilient projection or projections of the front component arranged above the anterior surface of the capsular bag. Therefore, the multicomponent intraocular lens can be held firmly to the capsular bag.

To that effect, the base component is firstly inserted through an opening or rhexis made in the anterior membrane of the capsular bag, a.k.a. front capsule. Then, a marginal portion of the front capsule is brought back onto the haptics. Next, during implantation of the front component, the resilient projection of the front component is engaged with the retaining member of the base component. Then, the distal end portion of the resilient projection is flexed frontwards from its natural position to be laid onto the marginal portion of the front capsule, so that the projection will resiliently urge the front capsule backwards. The combined effect of the base component haptic that backs the marginal portion of the front capsule from the inside at a first circumferential position and the resilient projection that urges the marginal portion backwards at a second, adjacent circumferential position is to create tensile stress in the front capsule around the opening. By reaction, by virtue of its positive tensile module, the front capsule resists the resilient force of the projection, so that a firm, non-sliding contact is created between the front capsule on the one hand, and the base component haptic and front component resilient projection on the other hand.

Two basic functions of the lens assembly are fixation of the MC-IOL to the capsulorhexis and fixation of the components together. Besides, the attachment mechanism of the herein presented system allows to mount and attach the components together inside the capsular bag. At this stage, the one or more attachment tabs of the front component already engaged the retaining member of the base component and are below the anterior surface of the capsulorhexis. Then the attachment tabs of the front component are moved anteriorly in order to capture the capsulorhexis. So at this point, the attachment tabs of the front component remain above the capsulorhexis whereas the haptics of the base component are beneath the capsulorhexis. In order to properly orient the axis of the base component, the surgeon then elevates, simultaneously, the one or more attachment tabs of the front component freeing up the capsulorhexis and simultaneously rotate the MC-IOL in the proper orientation. Finally, the attachment tabs are released onto the anterior surface of the capsulorhexis, capturing the capsulorhexis and preventing any rotation.

A number of different shapes can be employed for the retaining member of base component and attachment tab of front component which are intended to cooperate as an attachment device for attaching the front component to the base component. The or each attachment tab may have a cylindrical shape or other.

In an embodiment, the or each retaining member comprises a flange having an elongated slot the length of which extends in the circumferential direction around the central portion, wherein the attachment tab of the front component has a flat shape and passes through the slot of the flange. With such geometry, it is possible to provide a reliable attachment between the front component and base component whereas the flat shape of the flange favors flexibility in a thickness direction thereof.

In another embodiment, the attachment device includes a snap fastener, e.g. with a retaining member configured as a pin protruding on the front surface of the base component for engaging a corresponding recess in the attachment tab.

In embodiments, the front component may be made of a single component or as an assembly of several subcomponents, e.g. an assembly of a mid-lens and a top lens attached together or an assembly comprising a stack of multiple lenses. Embodiments of such assemblies are disclosed in WO-A-2011006008.

In an embodiment, the base component is implemented as a support component that serves as a fixed platform for carrying the front component is the eye. In that implementation, the central portion of the base component may be a hollow frame having a central aperture substantially aligned with the optical portion of the front component, for example as disclosed in FIG. 31 of WO-A-2012054854.

In an embodiment, the central portion of the base component comprises an optical portion.

In a preferred embodiment, the optical portion of the front component and/or the base component is substantially circular. The optical portion of the front component and/or the base component may also have different shapes, for example elliptical or other.

In an embodiment, the optical portion of the front component comprises a back surface turned towards the front surface of the optical portion of the base component, wherein the back surface of the optical portion of the front component comprises a peripheral contact portion that is laid directly on the front surface of the optical portion of the base component all around the optical portions and a central, recessed portion that is spaced from the front surface of the optical portion of the base component, so as to define a chamber between said front surface and said back surface.

In an embodiment, the front component comprises a through-hole that passes through a thickness of the optical portion to provide an access to the chamber from a front surface of the optical portion.

In an embodiment, the or each attachment tab comprises a through-hole suitable for inserting a hook or catching tool.

In an embodiment, the portion of the resilient projection is a distal end portion located at a distance from the optical portion of the front component.

A number of different shapes can be employed for the haptic and the attachment tab in order to provide the configuration of a back surface of the portion, e.g. distal end portion, of the resilient projection that is located backwards from the front surface of the haptic of the base component. The amount of bending deformation that is necessary to bring the resilient projection from its rest position to its operating position over the front capsule depends on the position of the projection at rest. In an embodiment, the front surface of the distal end of the resilient projection and the front surface of the haptic lie in a same plane perpendicular to the thickness direction of the base component. Thus, the amount of deformation necessary is similar to the thickness of the resilient projection. In an embodiment, the back surface of the distal end of the resilient projection and the back surface of the haptic lie in a same plane perpendicular to the thickness direction of the base component. Thus, the amount of deformation necessary is similar to the thickness of the haptic. In embodiments, the haptic and the resilient projection may have the same thickness or different thicknesses.

In an embodiment, the resilient projection at rest is angulated backwards in the thickness direction of the base component. In corresponding embodiments, the haptic of the base component at rest may be oriented transverse to the thickness direction of the base component, or angulated frontwards, or angulated backwards as well, e.g. with a lower angle than the resilient projection.

In an embodiment, the or each haptic of the base component at rest is angulated frontwards in the thickness direction of the base component. In corresponding embodiments, the resilient projection of the front component at rest may be oriented transverse to the thickness direction of the base component, or angulated backwards, or angulated frontwards as well, e.g. with a lower angle than the haptic.

A number of different shapes are suitable for the haptic or haptics of the base component. In particular, the base component may comprise at least one long haptic intended to engage an inner peripheral portion of a capsular bag of the human eye, in particular two long haptics extending in opposite directions to engage the capsular bag along a full diameter thereof. Alternatively or in addition, the base component may comprise at least one shorter haptic intended to remain at a distance from the inner peripheral portion of a capsular bag of the human eye. In embodiments, the longer and/or the shorter haptics may serve to tension the marginal portion of a front capsular membrane of the human eye in cooperation with the resilient attachment tab of the front component.

In an embodiment, the base component comprises a loop-shaped haptic having two branches extending from the circumferential side of the central portion away from the central portion at two circumferential positions located on both sides of the resilient projection in the circumferential direction, wherein each of the two branches of the loop-shaped haptic has an end portion which extends farther from the optical or central portions than the distal end of the resilient projection and which is curved along the circumferential direction towards the resilient projection, so that the end portions of the two branches meet to form a closed loop around the resilient projection as seen in a projection along the thickness direction. With this configuration, the non-sliding contact between the front capsule and the multicomponent intraocular lens can be made stronger because the loop-shaped haptic backs the marginal portion of the front capsule from the inside all around the resilient projection that urges the marginal portion backwards. Thus, a contact surface of the haptic with the front capsule is enlarged. Preferably, the loop-shaped haptic is a long haptic.

In an embodiment, the base component comprises a pair of haptics extending from the circumferential side of the optical portion away from the optical portion at two circumferential positions located on both sides of the resilient projection in the circumferential direction, wherein the resilient projection extends in a substantially radial position between the pair of haptics as seen in a projection along the thickness direction. With this configuration, the non-sliding contact between the front capsule and the multicomponent intraocular lens can be made stronger by alternating the haptics that back the marginal portion of the front capsule from the inside and the resilient projection that urges the marginal portion backwards. This configuration can be repeated in space around the multicomponent intraocular lens by providing a higher number of alternated haptics and resilient projections. This embodiment can be implemented with a pair of long or short haptics.

In an embodiment, the base component comprises a pair of retaining members, e.g. flanges, which are diametrically opposed with respect to the central portion of the base component and wherein the front component comprises a pair of attachment tabs which are diametrically opposed with respect to the optical portion of the front component.

In embodiments, the retaining members of the base component can be arranged at different positions, e.g. at aligned positions with the haptics of the base component in the circumferential direction or a offset positions from the haptics of the base component in the circumferential direction. Accordingly, the attachment tab of the front component may be at an adjacent or non-adjacent position with respect to the haptic of the base component in the circumferential direction.

In an embodiment, the base component comprises an annular rib protruding on the front surface of the base component in the thickness direction of the base component and arranged around the optical portion of the front component, wherein an inner diameter of the annular rib substantially matches an outer diameter of the optical portion of the front component. In an embodiment, the flange and the annular rib of the base component are made as a single piece. Such an annular rib is useful for inhibiting cellular growth between the optical portions of the front and base components, e.g. capsular cell growth known as pearl formation. Alternatively or in combination, a number of other measures can be employed to reduce pearl formation.

In an embodiment, the base component comprises an annular groove or annular rib formed on the front surface of the base component in the thickness direction of the base component and arranged around the central portion of the base component, wherein the front component comprises a corresponding annular rib or annular groove formed on the back surface of the front component. The annular rib is adapted to be engaged in the annular groove to attach the front component to the base component.

Ensuring a strong contact between the front component and base component helps also reduce Elschnig's pearl formation. The strength of the contact depends on different parameters relating to the geometry and the materials of the base and front components. For example, the larger the contact portion of the front component that is laid directly on the front surface of the optical portion of the base component, the stronger the contact. For the selection of materials, different approaches may be employed.

In an embodiment, the base component and the front component are both made of hydrophobic materials or the base component and the front component are both made of hydrophilic materials. In an embodiment, the base component and the front component are made of different materials, wherein a first component among the base component and the front component is made of a hydrophobic material and a second component among the base component and the front component is made of a hydrophilic material. By using materials having a similar or a different reaction to water, it is possible to adjust the interaction forces binding the two components. Hydrophobic materials may have a stronger effect for inhibiting cell growth.

The short or long haptic or haptics of the base component, especially the loop-shaped haptic, and the attachment tab whose back surface ends backwards from the front surface of the haptic form a catching device for catching a rim portion of the front capsule. In embodiments, the multicomponent intraocular lens may be provided with a plurality of such catching devices. However, sufficient stability of the multicomponent intraocular lens may be obtained by catching a single portion of the front capsule. In a corresponding embodiment, the multicomponent intraocular lens is provided with a single catching device, so that manufacturing and implantation are made easier.

In an embodiment, the front component comprises one single attachment tab whose back surface ends backwards from the front surface of at least one haptic of the base component, especially one single loop-shaped haptic of the base component, so as to catch one single portion of the front capsule.

The multicomponent intraocular lens may be employed to correct a number of optical impairments of the eye, e.g. myopia, presbyopia, astigmatism, spherical aberrations, higher order aberrations and the like. The visual correction may be performed by both the base component and the front component, each of which comprises an optical portion that carries a portion of the total optical correction to be applied. In another embodiment, the optical portion of the base component is absent or optically neutral and the front component carries the whole optical correction to be applied.

In an embodiment, the optical portion of the front component and/or base component is adapted to correct astigmatism, wherein the optical portion comprises an optical axis that characterizes the astigmatic correction, wherein the front component and/or base component further comprises an orientation mark to denote the optical axis of the optical portion, wherein the orientation mark is made of a material selected in the group of materials that absorb or reflect visible light and materials that are transparent to visible light and that absorb or reflect UV light, e.g. incorporated into the optical portion. In an embodiment, the orientation mark is a conformation of the front surface of the optical portion, e.g. a tiny groove or scratch.

With materials that are transparent to visible light and that absorb or reflect UV light, it is possible to provide an orientation mark that will not impact the sight of the patient while being able to be seen by a surgeon under UV lighting during implantation of the intraocular lens or afterwards, e.g. in a secondary operation. This orientation mark is visualized as well as in the operating room and also in the office.

In an embodiment, the front component and base component are foldable. In other embodiments, at least one of the optical portion of the front component and the central portion of the base component is stiff. In an embodiment, the whole base component is stiff.

Aspects of the invention are based on the idea of slightly catching, clamping, pinching, winding or tightening a rim of the capsular membrane between an attachment tab of a front component and at least one haptic of the base component in order to improve rotational stability of the MC-IOL used in posterior chamber implantation.

Aspects of the invention are based on the idea of ensuring exchangeability of the front component after healing.

Aspects of the invention are based on the idea of inhibiting cell growth between the base component and the front component.

BRIEF DESCRIPTION OF THE DRAWINGS

These and other aspects of the invention will be apparent from and elucidated with reference to the embodiments described hereinafter, by way of example, with reference to the drawings.

FIG. 9 is a perspective representation of a base lens in accordance with a fifth embodiment.

FIG. 10 is a perspective view of the MC-IOL in accordance with a fifth embodiment.

FIG. 11 is a plane top view of the MC-IOL in accordance with a sixth embodiment in use, in a state of engagement with the front capsule of an eye.

DETAILED DESCRIPTION OF THE EMBODIMENTS

Figure 1:
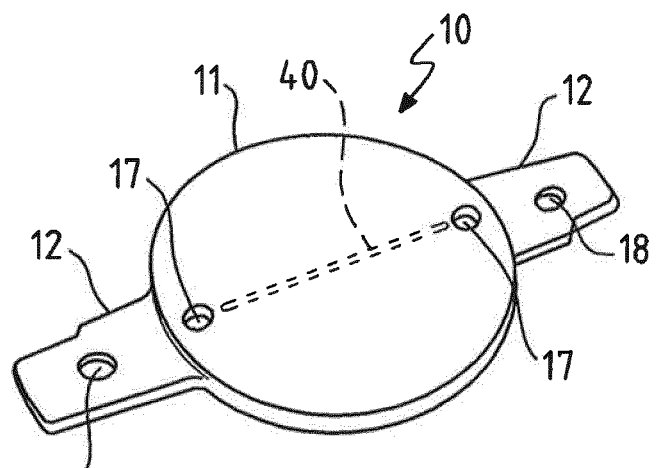
FIG. 1 is a perspective representation of a front lens of an MC-IOL in accordance with a first embodiment.
Figure 2:
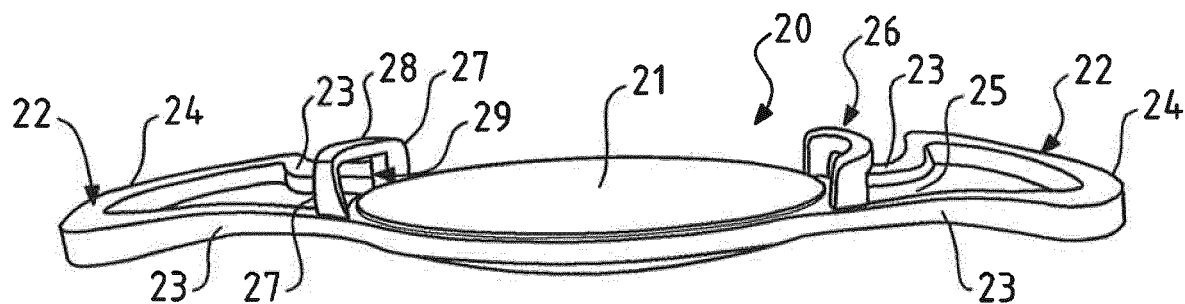
FIG. 2 is a perspective representation of a base lens of the MC-IOL in accordance with the first embodiment.
Figure 3:
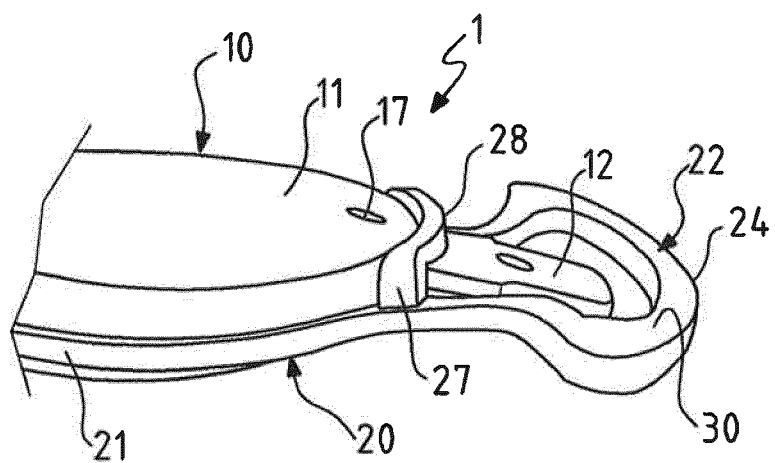
FIG. 3 is a partial perspective representation of the MC-IOL in accordance with the first embodiment, at rest.
Figure 4:
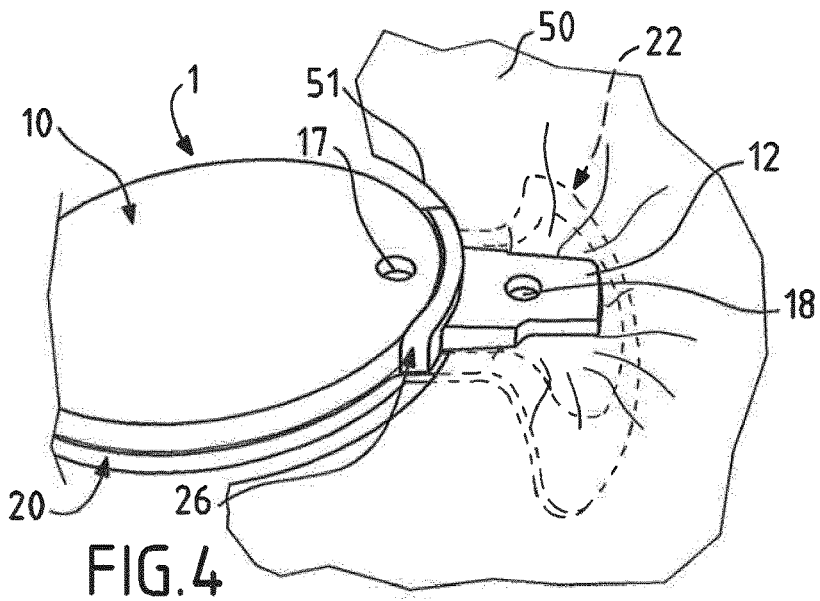
FIG. 4 is a partial perspective representation of the MC-IOL in accordance with the first embodiment in use, in a state of engagement with the front capsule of an eye.

With reference to FIGS. 1 to 4, an MC-IOL 1 in accordance with a first embodiment of the invention will now be described. The MC-IOL 1 consists of a front lens 10 shown on FIG. 1 and a base lens 20 shown on FIG. 2 and intended to receive the front lens 10. FIG. 3 shows the front lens 10 and base lens 20 in an assembled state of the MC-IOL 1 at rest. FIG. 4 schematically illustrates the assembled MC-IOL 1 in use engaged with a capsular membrane 50 of the eye.

The front lens 10 and the base lens 20 are thin, generally flat, foldable elements that can be manufactured from any suitable foldable materials, e.g. acrylic or silicone materials. Accordingly, the insertion of the front lens 10 and the base lens 20 into the eye requires an incision therein which is less than half as large as the larger diameter of the front lens 10 and base lens 20.

The front lens 10 includes a substantially circular optical portion that is made of a transparent material and resilient attachment tabs 12, here in the number of two, which protrude radially around the optical portion 11, i.e. perpendicularly to the thickness direction of the front lens 10. The attachment tabs 12 shown here are arranged at two diametrically opposed positions. The attachment tabs 12 may be made of the same material as the optical portion 11 or of a different material, which is not necessarily transparent. As visible on FIG. 3, the attachment tabs 12 are angulated backwards along the thickness direction at rest, so as to pass behind the front surface 30 of the base lens 20 in the assembled state of MC-IOL 1.

The optical portion 11 has a central thickness ranging from 0.1 millimeters to 0.4 millimeters, and a diameter ranging from 1.50 to 8.50 millimeters, but preferably is between 5.50 and 7.00 millimeters. The optical portion 11 features an optical aperture ranging from 3.0 millimeters to 7.0 millimeters, with a preferable optical aperture of 5.5 millimeters.

The base lens 20 includes a substantially circular optical portion 21 that may have similar, larger or smaller dimensions than the optical portion 11 and one or more haptics. In the embodiment shown, two long, loop-shaped haptics 22 are arranged at two diametrically opposed positions around the circular optical portion 21. In the embodiment shown, a loop-shaped haptic 22 extends in a plane perpendicular to the thickness direction of the optical portion 21. By convention, the thickness direction of circular optical portion 21 will be also referred to as vertical, whereas the plane perpendicular to the thickness direction of the optical portion 21 will be also referred to as horizontal. In service, the loop-shaped haptics 22 are intended to secure the base lens into the capsular bag of the eye by engaging an inner peripheral side of the capsular bag at two diametrically opposed positions.

More precisely, a loop-shaped haptic 22 includes two protruding arms 23 that are spaced from one another along the periphery of the optical portion 21 and that extend substantially parallel away from the optical portion 21, and a loop portion 24 connecting both protruding arms 23 at a distance from the periphery of the optical portion 21. Each protruding arm 23 comprise a straight, proximal portion attached to the periphery of the optical portion 21 and a distal portion that curves away from the space 25 separating the proximal portions of the two protruding arms 23 at an angle of about 60° to 90°. The loop portion 24 extends as an arc of circle substantially parallel to the periphery of the optical portion 21 between the distal ends of the two protruding arms 23.

As visible on FIG. 2, each loop-shaped haptic 22 carries an attachment flange 26 for engaging an attachment tab 12 of the front lens 10. More precisely, the attachment flange 26 comprises two vertical arms 27. Each vertical arm 27 is arranged on the proximal portion of a protruding arm 23 on the edge of the optical portion 21. An horizontal arm 28 bridges the gap between the two vertical arms 27 to define a substantially rectangular slot 29 in the attachment flange 26. The horizontal arm 28 has a curved shape, e.g. as an arc of circle substantially parallel to the periphery of the optical portion 21.

FIG. 3 shows the MC-IOL 1 in the assembled state at rest, i.e. when no external forces are applied to it. The optical portions 11 and 21 are laid parallel against one another while each attachment tab 12 is inserted through the slot 29 of a corresponding attachment flange 26. The attachment tab 12 has a shorter length than the distance between loop portion 24 and optical portion 21, so that the protruding end of attachment tab 12 is entirely received in the space within the loop-shaped haptic 22. Due to the backward angulation of attachment tab 12, the protruding end of attachment tab 12 plunges through space 25 separating the proximal portions of the two protruding arms 23 so that an end portion of attachment tab 12 is located backwards from the front surface 30 of haptic 22.

FIG. 4 shows schematically the MC-IOL 1 in service when implanted in the posterior chamber of an eye. The anterior side of the capsular bag is partially shown at numeral 50. It is recalled that the surgeon makes a substantially circular opening 51 called capsulo-rhexis in the front capsule 50 to remove the natural lens. This rhexis has a diameter somewhat bigger than the optical portions of the lenses and much smaller than the diameter of the capsular bag, to ensure that MC-IOL 1 is trapped within the bag. The base lens 20 is then inserted through the same opening 51. Then, a marginal portion of the front capsule 50 is laid over the front surface of haptics 22. Next, the front lens 10 is inserted and the attachment tabs 12 of the front lens 10 are engaged through the slots of the flanges 26 of the base lens 20. At that time or subsequently, the attachment tabs 12 are flexed frontwards from their natural position to be laid onto the marginal portion of the front capsule 50. In that state, the attachment tabs 12 resiliently urge the front capsule 50 backwards due to their intrinsic elasticity. Therefore, the front capsule 50 is held firmly between the front surface of each haptic 22 and the back surface of each attachment tab 12 in a manner similar to a sheet of paper clamped by a paper clip.

An important outcome of the above procedure is that the MC-IOL 1 is held to the capsular bag and cannot freely rotate in the eye after implantation. Therefore, a steady and durable orientation is obtained, in particular around the vertical axis which corresponds to the central axis of the pupil. Such stability is especially important for achieving certain anisotropic optical corrections such as correction of astigmatism.

The clamping of the front capsule 50 may be obtained at two diametrically opposed locations using both attachment tabs 12 and both haptics 22 in a symmetrical embodiment.

This lens design requires a two-handed or two-instrument technique to rotate the lens at the time of the primary surgery to properly align the axis of astigmatism. As visible on FIGS. 1 to 4 the front lens 10 may comprise one or more holes 17 around the optical portion 11 and one or more holes 18 in the attachment tabs 12 to facilitate manipulation of the front lens 10 during implantation. Tools (not shown) engaged in the holes 17 or 18 make it possible to grip the front lens 10 without damaging it.

Alternatively, an asymmetrical embodiment makes it possible to clamp the front capsule 50 at a single location between one attachment tab 12 and one corresponding haptic 22, whereas the other attachment tab 12 and the other haptic 22 do not have any clamping effect, e.g. are parallel. This alternative lens design only requires a one-handed or one-instrument technique to rotate the lens.

In the above embodiment, each attachment tab 12 cooperates with a corresponding flange 26 to attach the front lens 10 to the base lens 20 in a releasable manner. In other words the two attachment tabs 12 and the two corresponding flanges 26 constitute two releasable attachment devices. In modified embodiments, similar attachment devices may be provided at a higher number of positions around the optical portions. In a modified embodiment, the whole MC-IOL comprises only one attachment device at only one position.

Figure 5:
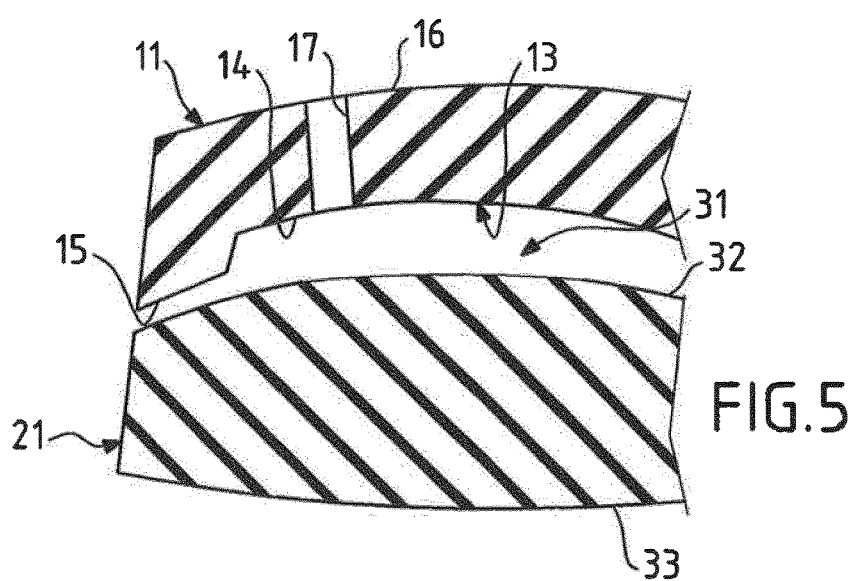
FIG. 5 is a sectional view of the MC-IOL in accordance with the first embodiment along a diameter of the optical portions.

FIG. 5 shows a cross-section of the MC-IOL 1 through the optical portions 11 and 21. A chamber 31 is defined between the optical portions 11 and 21 due to the shape of the back surface 13 of optical portion 11. Namely, back surface 13 includes a central recessed portion 14 surrounded by a flat annular portion 15 that abuts directly against the front surface 32 of base lens 20 in the attached state. As a result, four surfaces are available in this embodiment for shaping as a function of the desired optical corrections: front surface 16 and back surface 13 of front lens 10, and front surface 32 and back surface 33 of base lens 20.

Hole 17 shown on FIG. 5 communicates with chamber 31 so that fluid pressure can be injected through it to facilitate detachment of the front lens 10 from the base lens 20, e.g. in a secondary operation. By contrast, the contact between annular portion 15 and front surface 32 holds the two lenses together through molecular phenomena, e.g. cohesion or adhesion depending on materials employed.

A strong contact between the front lens 10 and the base lens 20 is desirable to prevent cellular growth between both lenses. Other means may be employed for that purpose as will now be explained with reference to FIGS. 6 to 8.

Figure 6:
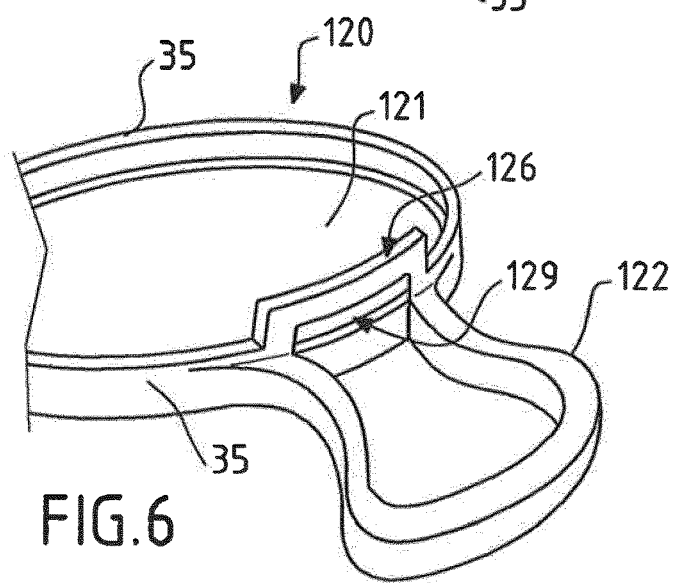
FIG. 6 is a partial perspective representation of a base lens in accordance with a second embodiment.

In the embodiment of FIG. 6, elements that are identical or similar to those of FIG. 2 are designated by the same numeral increased by 100. In base lens 120, the optical portion is surrounded by an annular rib 35. In use, the front lens optical portion (not shown) is inserted or snap-fitted within the annular rib 35. The annular rib 35 is intended to fit closely the periphery of the front lens optical portion to also inhibit cell growth between both lenses. In the example shown, flange 126 is made continuous with the annular rib 35 and the horizontal arm of flange 126 is higher than the top of annular rib 35 in the thickness direction.

Figure 7:
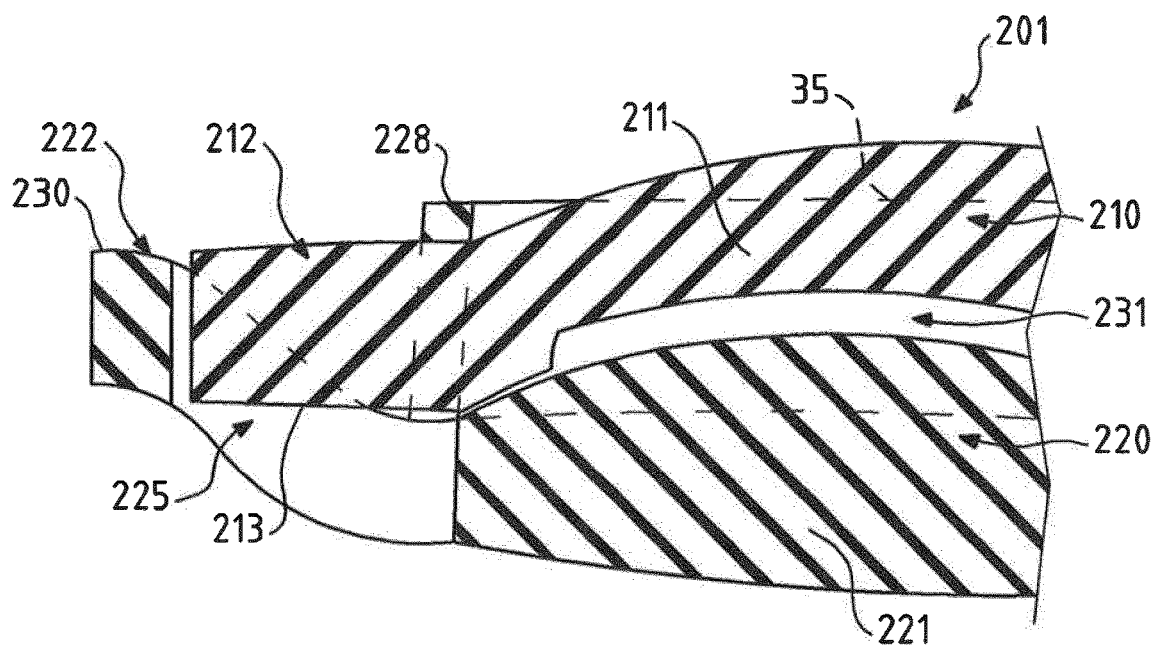
FIG. 7 is a sectional view of the MC-IOL in accordance with a third embodiment along a diameter of the optical portions.

In the embodiment of FIG. 7, elements that are identical or similar to those of FIGS. 1-5 are designated by the same numeral increased by 200. Similar to base lens 120, base lens 220 has an annular rib 35 surrounding the optical portion 221. In that case, the horizontal arm 228 is aligned with the top of annular rib 35 in the thickness direction.

Loop-shaped haptic 222 is angulated frontwards in the thickness direction. By contrast, in the example shown, attachment tab 212 extends horizontally from the optical portion 211 of the front lens 210 so that it ends within the inner space 225 of loop-shaped haptic 222. Namely, at rest, a back surface 213 of attachment tab 212 is behind the front surface 230 of haptic 222. In use, the MC-IOL 201 is locked to the capsular bag in the same manner as above, by flexing the attachment tab 212 frontward above the anterior membrane laid onto loop-shaped haptic 222.

Figure 8:
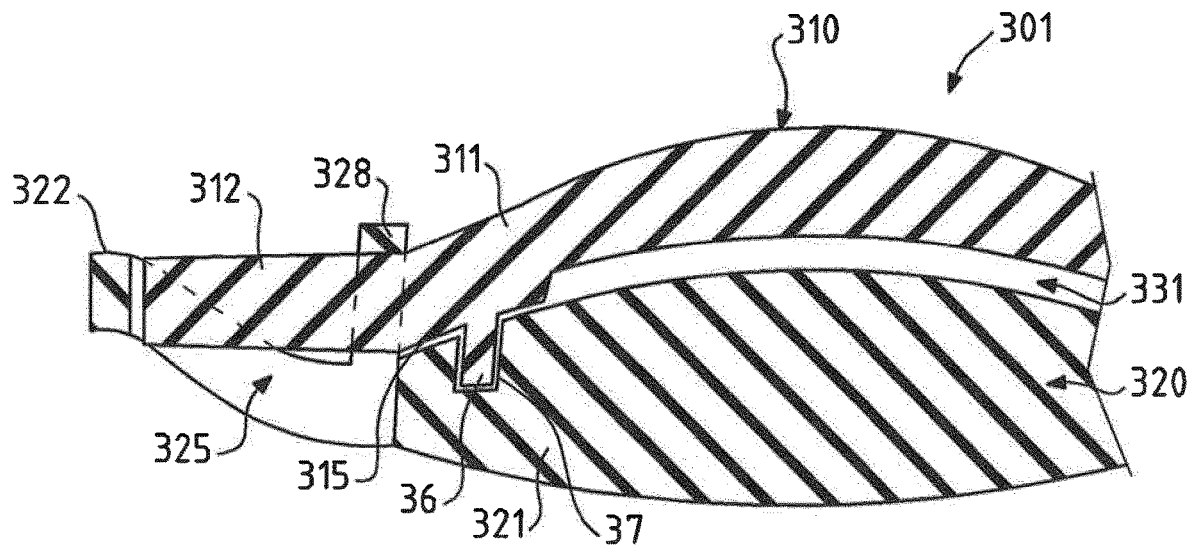
FIG. 8 is a sectional view of the MC-IOL in accordance with a fourth embodiment along a diameter of the optical portions.

In the embodiment of FIG. 8, elements that are identical or similar to those of FIGS. 1-5 are designated by the same numeral increased by 300. Base lens 320 comprises an annular groove 37 surrounding the optical portion 321. Front lens 310 comprises an annular rib 36 protruding backward from contact surface 315 and engaged in groove 37. This arrangement also inhibits cell growth between both lenses. Alternatively, the groove may be arranged on the front lens and the corresponding rib may be arranged on the base lens. For the rest, the geometry is similar to FIG. 7.

From FIGS. 5 to 8, it will be understood that different means of inhibiting cell growth and pearl formation between the lenses can be combined in diverse manners.

Although the above-described base lenses have loop-shaped haptics, it will be understood that modified embodiments of the base lens may comprise haptics in different numbers and in different shapes. As an illustration, FIG. 9 shows an embodiment in which elements that are identical or similar to those of FIG. 2 are designated by the same numeral increased by 400. Base lens 420 includes optical portion 421 and four protruding haptics 422 that are spaced from one another along the periphery of the optical portion 421 and extend horizontally away from the optical portion 421. Each haptic 422 includes a straight, proximal portion 423 attached to the periphery of the optical portion 421 and a distal portion 39 that curves away from the adjacent haptic 422 at an angle of about 60° to 90°. In the example shown, the proximal portions 423 of all four haptics 422 are substantially parallel. The base lens 420 can be employed with the front lens 10 in the same manner.

FIG. 1 also illustrates the concept of an orientation mark 40 mechanically or chemically inserted or formed in the front lens 10 at the time of manufacturing to indicate an optical axis for astigmatic correction, so that the surgeon can orient properly the MC-IOL 1 within the eye. The orientation mark 40 is preferably made of a material or chemical dye visible by the surgeon under ultraviolet light, e.g. with the help of a UV lamp. Alternatively, orientation mark 40 is made as a local unevenness of the front surface that will be visible by the surgeon under oblique visible light, e.g. with the help of a slit lamp. In all cases, the orientation mark 40 is designed to remain substantially invisible from the patient.

The attachments tabs 12 may not remain visible at all times by the surgeon during operations. The orientation mark 40 is preferably aligned with the attachments tabs 12 as an indication of their location. In an embodiment, a similar orientation mark may also appear on the base lens.

In the embodiment of FIG. 10, elements that are identical or similar to those of FIGS. 1-3 are designated by the same numeral increased by 500. The base lens 520 is shown in solid line whereas the front lens 510 is shown in phantom line. The two loop-shaped haptics 522 are connected to the top of the two flanges 526, so that the loop-shaped haptics 522 are offset frontward with respect to the optical portion 521. Thanks to this feature, the loop-shaped haptics 522 maintain the optical portion 521 further backwards into the eye, so that the MC-IOL 501 occupies less space in the eye sulcus, which facilitates the surgeon's intervention. This embodiment is also applicable to other haptic shapes.

FIG. 10 shows the front lens 510 in service, i.e. with the attachment tabs 512 flexed frontwards to lie on the front capsule (not shown). At rest, the attachment tabs 512 may be parallel to the optical portion 511, so that they lie entirely under the loop-shaped haptics 522.

In the embodiment of FIG. 11, elements that are identical or similar to those of FIGS. 1-4 are designated by the same numeral increased by 600. Here, the base lens 620 has four shorter haptics 55 in addition of the two loop-shaped haptics 622. The shorter haptics 55 are arranged horizontally around the central portion of the base lens 620 at different circumferential locations from the loop-shaped haptics 622, i.e. e.g. at +45° and −45° of each loop-shaped haptic 622. In addition, the flanges 626 are offset by 90° around the base lens compared to the embodiment of FIG. 2, so that each flange 626 is located at mid-distance between two shorter haptics 55.

The front lens 610 is configured in the same manner as in FIG. 3, except that it is also turned by 90° around the base lens in accordance with the modified position of the flanges 626. Given that the attachment tabs 612 are angulated backwards at rest, they operate to catch the marginal portion of the front capsule 650 in the same manner as was described in FIG. 4, with the difference that the pair of adjacent shorter haptics 55 are now supporting the front capsule 650 against the resilient force of an attachment tab 612. The loop-shaped haptics 622 which are located farther from the attachment tabs 612 play here a lesser role in the clamping of the front capsule 650.

In modified embodiments, the shorter haptics 55 may be angulated frontwards or backwards. The shorter haptics 55 may be provided in a different number and at different locations to exert a similar clamping function.

Put differently, the loop-shaped haptics 622 and the shorter haptics 55 have different functions. Loop-shaped haptics 622 serve to engage a periphery of the capsular bag to hold the base lens 620 in the capsular bag, whereas shorter haptics 55 serve to engage a marginal portion of the front capsule around the rhexis 651 in cooperation with the attachment tabs 612. By contrast, both functions may be combined in the haptics 22 of FIG. 4.

Figure 12:
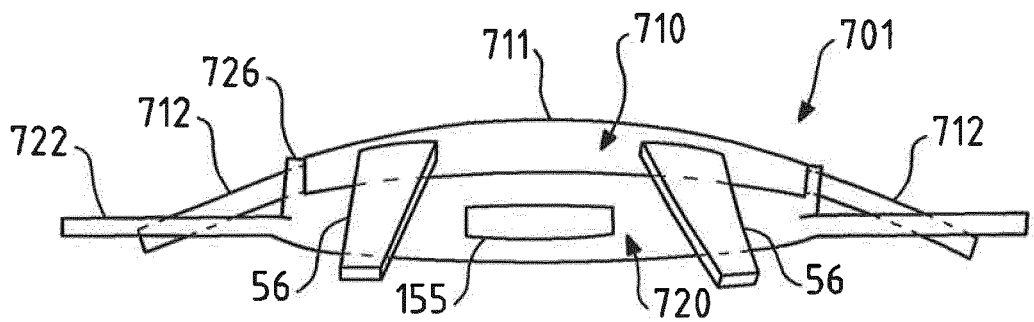
FIG. 12 is a perspective view of the MC-IOL in accordance with a seventh embodiment.
Figure 13:
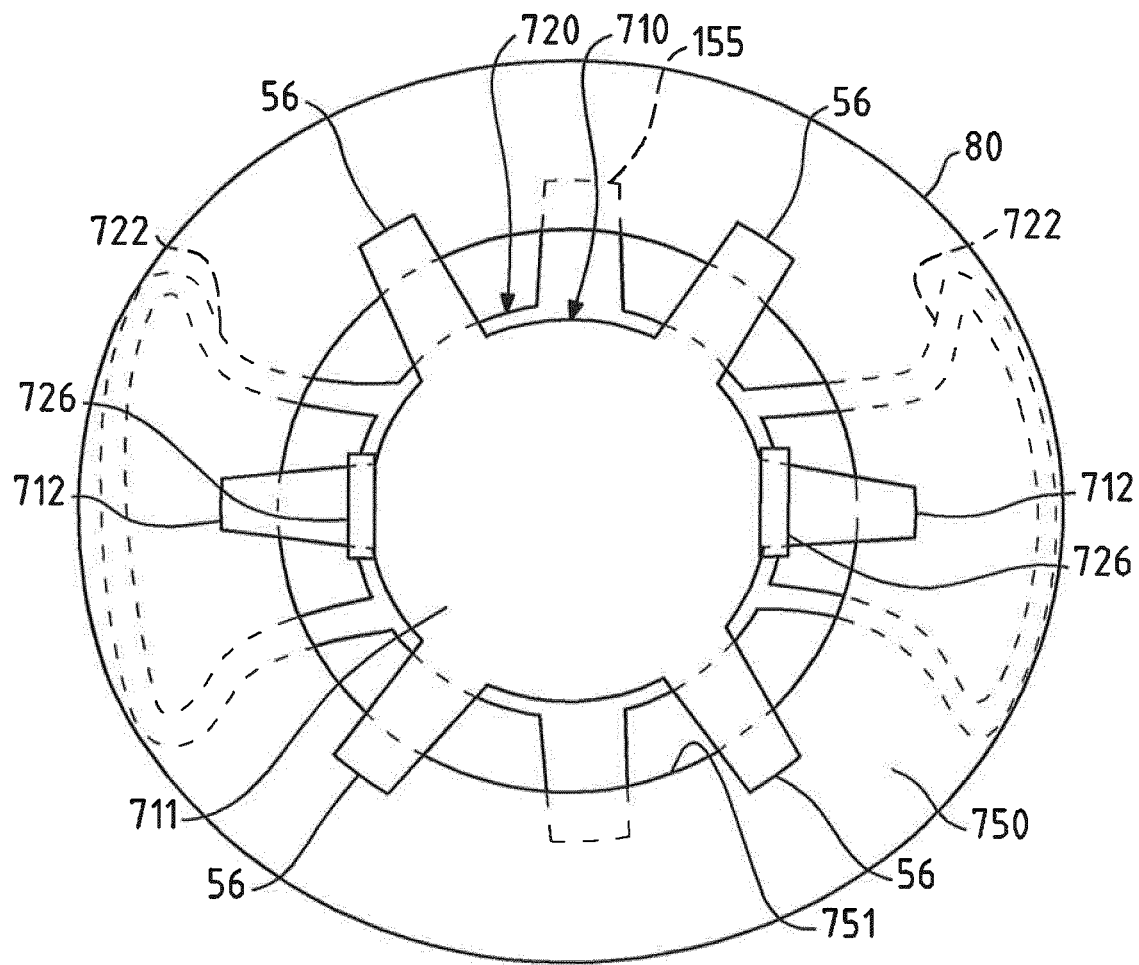
FIG. 13 is a plane top view of the MC-IOL of FIG. 12 in use, in a state of engagement with the front capsule of an eye.

Turning now to FIGS. 12 and 13, elements that are identical or similar to those of FIGS. 1-4 are designated by the same numeral increased by 700. In the MC-IOL 701, the base lens 720 has two shorter haptics 155 in addition of the two loop-shaped haptics 722. The shorter haptics 155 are arranged horizontally around the central portion of the base lens 720 at different circumferential locations from the loop-shaped haptics 722, i.e. at 90° of the loop-shaped haptics 722. The loop-shaped haptics 722 of base lens 720 and the attachment tabs 712 of front lens 710 operate in the same manner as in FIG. 4 to catch the marginal portion of the front capsule 750 of capsular bag 80. In addition, front lens 710 comprises four further resilient projections 56 arranged around the central portion of the front lens 710 at different circumferential locations from the attachment tabs 712, i.e. e.g. at +45° and −45° of each attachment tab 712. The further resilient projections 56 are angulated backwards to exert a clamping of the front capsule 750 in cooperation with the shorter haptics of base lens 720. Namely, a shorter haptic 155 backs the front capsule 750 from inside between two resilient projections 56 that are urged backwards by their intrinsic elasticity. Due to the combined effect of the loop-shaped haptics 722 and attachment tabs 712 on the one hand, and shorter haptics 155 and resilient projections 56 on the other hand, a rotational orientation of the MC-IOL 701 in the capsular bag is secured very stable manner. It must be noted that the size of the rhexis 751 is exaggerated on FIG. 13 for the sake of clarity.

The total frictional force between the MC-IOL and the front capsule depends on both the total contact surface of the above recited elements with the front capsule and the intensity of the resilient tensioning force exerted by the resilient projections and tabs. Therefore, for a given stability, a larger surface makes it possible to employ a lower force and conversely. The tensioning forces exerted on the capsular bag must be compatible with its natural resistance. MC-IOL 701 is especially suited for augmenting the contact surface.

In modified embodiments, the shorter haptics 155 may be angulated frontwards or backwards. The shorter haptics 155 and resilient projections 56 may be provided in a different number and at different locations to exert a similar clamping function.

The invention is not limited to the described embodiments. The appended claims are to be construed as embodying all modification and alternative constructions that may be occurred to one skilled in the art, which fairly fall within the basic teaching here, set forth.

The use of the verb "to comprise" or "to include" and its conjugations does not exclude the presence of elements or steps other than those stated in a claim. Furthermore, the use of the article "a" or "an" preceding an element or step does not exclude the presence of a plurality of such elements or steps.

In the claims, any reference signs placed between parentheses shall not be construed as limiting the scope of the claims.

The invention claimed is:

1. A multicomponent intraocular lens implantable in an optical system of a human eye, the multicomponent intraocular lens comprising:
   a base component having a front surface intended to be turned towards a front side of the human eye and a back surface opposed to the front surface in thickness direction of the base component and intended to be turned towards a back side of the human eye, the base component comprising a central portion and a haptic which extends from a circumferential side of the central portion away from the central portion, the base component further comprising a retaining member located at a periphery of the central portion and protruding on the front surface of the base component beyond a front surface of the central portion in the thickness direction of the base component, and
   a front component comprising an optical portion arranged in front of the front surface of the central portion of the base component, the front component further comprising an attachment tab which extends from a circumferential side of the optical portion of the front component away from the optical portion of the front component and engages the retaining member for attaching the front component to the base component, wherein the attachment tab of the front component comprises a resilient projection that protrudes away from the optical portion of the front component beyond the retaining member, wherein a portion of the resilient projection is located at a non-overlapping position with respect to the haptic of the base component in a circumferential direction around the central portion of the base component, wherein the portion of the resilient projection has a back surface which is located backwards from a front surface of the haptic of the base component in the thickness direction of the base component.

2. The multicomponent intraocular lens of claim 1, wherein the retaining member comprises a flange having an elongated slot the length of which extends in the circumferential direction around the central portion, wherein the attachment tab of the front component has a flat shape and passes through the slot of the flange.

3. The multicomponent intraocular lens of claim 1, wherein the central portion of the base component comprises an optical portion of the base component.

4. The multicomponent intraocular lens of claim 3, wherein the optical portion of the front component comprises a back surface turned towards the front surface of the optical portion of the base component, wherein the back surface of the optical portion of the front component comprises a peripheral contact portion that is laid directly on the front surface of the optical portion of the base component all around the optical portions and a central, recessed portion that is spaced from the front surface of the optical portion of the base component, so as to define a chamber between said front surface of the optical portion of the base component and said back surface of the optical portion of the front component.

5. The multicomponent intraocular lens of claim 4, wherein the front component comprises a through-hole that passes through a thickness of the optical portion to provide an access to the chamber from a front surface of the optical portion.

6. The multicomponent intraocular lens of claim 1, wherein the attachment tab comprises a through-hole suitable for inserting a hook or catching tool.

7. The multicomponent intraocular lens of claim 1, wherein the portion of the resilient projection is a distal end portion located at a distance from the optical portion of the front component.

8. The multicomponent intraocular lens of claim 1, wherein the resilient projection at rest is angulated backwards in the thickness direction of the base component.

9. The multicomponent intraocular lens of claim 1, wherein the haptic of the base component at rest is angulated frontwards in the thickness direction of the base component.

10. The multicomponent intraocular lens of claim 1, wherein the haptic of the base component is a long haptic intended to engage an inner peripheral portion of a capsular bag of the human eye.

11. The multicomponent intraocular lens of claim 1, wherein the base component comprises a loop-shaped haptic having two branches extending from the circumferential side of the central portion away from the optical central at two circumferential positions located on both sides of the resilient projection in the circumferential direction, wherein each of the two branches of the loop-shaped haptic has an end portion which extends farther than a distal end of the resilient projection and which is curved along the circumferential direction towards the resilient projection, so that the end portions of the two branches meet to form a closed loop around the resilient projection.

12. The multicomponent intraocular of claim 1, wherein the base component comprises a pair of haptics extending from the circumferential side of the central portion away from the central portion at two circumferential positions located on both sides of the resilient projection in the circumferential direction, wherein the resilient projection extends in a substantially radial position between the pair of haptics as seen in a projection along the thickness direction.

13. The multicomponent intraocular lens of claim 1, wherein the base component comprises a pair of retaining members which are diametrically opposed with respect to the central portion of the base component and wherein the front component comprises a pair of attachment tabs which are diametrically opposed with respect to the optical portion of the front component.

14. The multicomponent intraocular lens of claim 1, wherein the base component comprises an annular rib protruding on the front surface of the base component in the thickness direction of the base component and arranged around the optical portion of the front component, wherein an inner diameter of the annular rib substantially matches an outer diameter of the optical portion of the front component.

15. The multicomponent intraocular lens of claim 1, wherein the optical portion of the front component is adapted to correct astigmatism, wherein the optical portion comprises an optical axis that characterizes the astigmatic correction, wherein at least one of the front component or the base component further comprises an orientation mark to denote the optical axis of the optical portion, wherein the orientation mark is either made of a material selected in the group of materials that absorb or reflect visible light and materials that are transparent to visible light and that absorb or reflect ultraviolet (UV) light or the orientation mark is a conformation of the front surface of the optical portion.

16. The multicomponent intraocular lens in accordance with claim 1, wherein the resilient projection comprises an internal wall defining an opening within the resilient projection beyond the retaining member.

17. The multicomponent intraocular lens in accordance with claim 1, wherein the resilient projection extends into a space proximate the haptic to hold a front capsule of the human eye between the front surface of the haptic and the back surface of the resilient projection.

* * * * *